United States Patent
Madura

(10) Patent No.: US 8,183,047 B2
(45) Date of Patent: May 22, 2012

(54) METHODS OF DETECTING MASTITIS BY LEVELS OF PROTEASOMES

(75) Inventor: Kiran Madura, Bridgewater, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 160 days.

(21) Appl. No.: 12/738,340

(22) PCT Filed: Oct. 20, 2008

(86) PCT No.: PCT/US2008/080514
§ 371 (c)(1),
(2), (4) Date: Apr. 16, 2010

(87) PCT Pub. No.: WO2009/052504
PCT Pub. Date: Apr. 23, 2009

(65) Prior Publication Data
US 2010/0210022 A1    Aug. 19, 2010

Related U.S. Application Data

(60) Provisional application No. 60/999,495, filed on Oct. 18, 2007.

(51) Int. Cl.
*G01N 33/04* (2006.01)
*C12Q 1/37* (2006.01)

(52) U.S. Cl. ............. 436/23; 436/86; 436/94; 435/6.18; 435/7.4; 435/24; 435/287.1

(58) Field of Classification Search .......... None
See application file for complete search history.

(56) References Cited

U.S. PATENT DOCUMENTS

| 2003/0092116 A1 | 5/2003 | Chun et al. ............ 435/69.1 |
| 2006/0124064 A1 | 6/2006 | Fullam et al. ........... 119/14.02 |
| 2008/0226554 A1 * | 9/2008 | Colgan et al. ........... 424/9.1 |
| 2009/0246794 A1 * | 10/2009 | Madura et al. .......... 435/7.1 |

OTHER PUBLICATIONS

Larsen, L. B. et al. "Proteases and protein degradation in milk from cows infected with *Streptococcus uberis*," International Dairy Journal 14 (2004) 899-907.*

Bachmir, A. and Varshaysky, A. "The Degradation Signal in a Short-lived Protein" Cell 1989 vol. 56 (6): 1019-1032.

Boulanger et al. "Increased Nuclear Factor κB Activity in Milk Cells of Mastitis-Affected Cows" J. Dairy Sci. 2003 vol. 86 (4): 1259-1267.

DeMartino et al. "PA700, an ATP-dependent Activator of the 20 S Proteasome, Is an ATPase Containing Multiple Members of a Nucleotide-binding Protein Family" The Journal of Biological Chemistry 1994 vol. 269 (33): 20878-20884.

* cited by examiner

*Primary Examiner* — Yelena G Gakh
*Assistant Examiner* — Michelle Adams
(74) *Attorney, Agent, or Firm* — Licata & Tyrrell P.C.

(57) ABSTRACT

Method and systems for determining if one or more animals has mastitis and for monitoring animals and the quality of the milk they produce are disclosed. Systems and test assays disclosed are used to determine the quantity of proteasomes and proteins thereof, the activity of proteasome enzymes, the quantity of proteasome bound and regulating proteins, and the quantity of ubiquinated protein. Components and reagents for use in the systems and assays are also disclosed.

12 Claims, 6 Drawing Sheets

Sunshine and R-Dale are young healthy.
Cow1 was chronic infected.
Cow2 was injured.
Cow3 and 4 were suspicious and under observation.

Figure 6

| | Type (clone) | h | r | m | rb | y | misc | WB | IP | IHC | Cat # |
|---|---|---|---|---|---|---|---|---|---|---|---|
| Anti-Rpn2 | mAb (112-1) | y | | | | | | y | x | | PW9270 |
| Anti-Rpn5 | rabbit pAb | | | | | | at | y | | | PW0450 |
| Anti-Rpn6 | rabbit pAb | | | | | | at, cf | y | | | PW8370 |
| Anti-Rpn7 | rabbit pAb | y | | | | y | | y | | | PW8225 |
| Anti-Rpn8 | sheep pAb | y | | | | | | y | | y | PW8180 |
| Anti-Rpn10 | mAb (S5a-18) | y | | | | | | y | y | y | PW9250 |
| Anti-Rpn11 | rabbit pAb | y | | | | | | y | | | PW9625 |
| Anti-Rpn12 | rabbit pAb | y | | | | | | y | | y | PW8815 |
| Anti-Rpn12 | mAb (p31-27) | y | | | | | | y | x | y | PW8835 |
| Anti-Rpn12 | mAb (p31-3e) | y | | | | | | x | | y | PW9260 |
| Anti-Rpn12 | rabbit pAb | | | | | | at | y | | | PW0440 |

Caption: Antibodies to 19S Regulator non-ATPase Subunits

SEQUENCE LISTING

```
<160> NUMBER OF SEQ ID NOS: 7

<210> SEQ ID NO 1
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Blocked with succinimide
<220> FEATURE:
<221> NAME/KEY: MISC_FEATURE
<222> LOCATION: (8)..(8)
<223> OTHER INFORMATION: Labeled with 7-amino-4-methylcoumarylamide

<400> SEQUENCE: 1

Arg Pro Phe His Leu Leu Val Tyr
1               5

<210> SEQ ID NO 2
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
```

```
<222> LOCATION: (1)..(1)
<223> OTHER INFORMATION: Blocked with succinimide
<220> FEATURE:
<221> NAME/KEY: MISC_FEATURE
<222> LOCATION: (4)..(4)
<223> OTHER INFORMATION: Labeled with 7-amino-4-methylcoumarylamide

<400> SEQUENCE: 2

Leu Leu Val Tyr
1

<210> SEQ ID NO 3
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Labeled with 7-amino-4-methylcoumarylamide

<400> SEQUENCE: 3

Gly Pro Leu Glu
1

<210> SEQ ID NO 4
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION, Nle
<220> FEATURE:
<221> NAME/KEY: MOD_RES
<222> LOCATION: (3)..(3)
<223> OTHER INFORMATION: Nle
<220> FEATURE:
<221> NAME/KEY: MISC_FEATURE
<222> LOCATION: (4)..(4)
<223> OTHER INFORMATION: Labeled with 7-amino-4-methylcoumarylamide

<400> SEQUENCE: 4

Leu Pro Leu Glu
1

<210> SEQ ID NO 5
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 5
auuuaauuua auuuaauuua                                                   20

<210> SEQ ID NO 6
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
```

```
<223> OTHER INFORMATION: ACETYLATION, Nle
<220> FEATURE:
<221> NAME/KEY: MOD_RES
<222> LOCATION: (3)..(3)
<223> OTHER INFORMATION: Nle
<220> FEATURE:
<221> NAME/KEY: MISC_FEATURE
<222> LOCATION: (4)..(4)
<223> OTHER INFORMATION: Labeled with 7-amino-4-methylcoumarylamide

<400> SEQUENCE: 6

Leu Pro Leu Asp
1

<210> SEQ ID NO 7
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Labeled with 7-amino-4-methylcoumarylamide

<400> SEQUENCE: 7

Gly Pro Leu Asp
1
```

METHODS OF DETECTING MASTITIS BY LEVELS OF PROTEASOMES

This application is the national phase under 35 U.S.C. §371 of PCT International Application No. PCT/US2008/080514, filed Oct. 20, 2008, which claims priority to U.S. Provisional Application No. 60/999,495 filed Oct. 18, 2007, which are incorporated herein by reference.

FIELD OF THE INVENTION

The invention relates to methods of diagnosing mastitis and assessing milk quality by detecting the level and activity of proteasomes and proteasome-associated factors present, and systems, components and reagents for performing such methods.

BACKGROUND OF THE INVENTION

Mastitis is a general term that describes inflammation in the milk glands and tissue lining the mammary gland/udder. Inflammation is a cellular- and organ-specific response to injury that can arise from a number of environmental events and pathogenic agents. Mastitis can be induced by physical injury (such as that caused by the milking apparatus), and from bacterial and fungal infections. Infections of the teats, ducts and udders might be caused by mycoplasma, pseudomonas, *staphylococcus* and *streptococcus*, as well as coliforms such *Escherichia coli*. Probably more than a dozen different bacterial species, in addition to yeast and fungi, can cause mastitis in cow, sheep, goat and other farm animals. Yeast and fungal infections yield a sub-clinical form of infection and therefore may go undetected. However, it is not known if yeast/fungi can aggravate infection caused by a coincident bacterial infection.

The living environment of dairy cows is conducive to infection, since the soil and manure are rich sources of bacteria. The animals are in frequent contact with the soil, and this is evident when one compares natural fluctuations in the level of sub-clinical infections during wet and dry seasons. (Wet environment cause higher levels of SCC values). Furthermore, the milking process is itself highly conducive to cross contamination. Therefore, animal management procedures that promote good hygiene, replacement of bedding, and careful handling of the milking apparatus, play a key role in controlling the incidence of mastitis. Separation of infected animals, clean handling techniques, and well fitting vacuum suction cups can play an important role in minimizing the incidence of infection. Treatment of the affected animal includes antibiotics to eliminate the bacteria, and anti-inflammatory agents to reduce swelling.

The four teats drain separate compartments (quarters) in the udder, and the infection can migrate from one quarter to another in a single animal. Additionally, animal-to-animal and human contact can also extend the infection to other animals in the milk line. These issues are of considerable concern, since the milking process typically results in the collection of milk from many animals (50-200) in a common reservoir (bulk tank). Not surprisingly, a single heavily infected animal can compromise the quality of the entire milk output from a dairy facility. Analysis of samples from a local dairy showed that a single cow could contribute up to ~50% of the total somatic cell count in the reservoir that collected milk from 53 animals. This high SCC value has a direct negative effect on the price the dairyman receives for the milk, and affects the price he can garner until the next testing cycle (typically once a month). In contrast, a low SCC value can earn the dairyman a premium price, that is supplemented to the standard price.

The reduced milk output, poor milk quality, veterinary and health impact have a significant negative impact on the viability and productivity in dairy farms, in part because the animal continues to be fed, milked and chaperoned as the other animals, although its milk is discarded. Culling chronically infected, unresponsive animals is a prudent measure, as the burden of lost milk, contaminated milk, and veterinary expenses mount. In this regard, the technologies developed and described herein are expected to contribute to improving early diagnostics, minimizing cross-contamination, sequestering problematic animals, and monitoring efficacy of treatment.

The standard assay for measuring mastitis in the dairy industry is to count the number of cells (originating from the cow), in the milk. This estimate is termed the somatic cell count (SCC). Specifically, the SCC reflects the levels of cells, including immune cells, such as leukocytes that are released from the lining and tissues of the udder of the infected animal, into the udder cavity. Although these cells are present in the milk, it is difficult to estimate their levels due to the difficulty of visualizing clear cells in the turbid milk suspension. The number of somatic cells in a given volume of milk (typically 1 ml) provides a semi-quantitative estimate of the degree of infection, because unaffected animals typically have low SCC levels. However, the SCC value is a gauge of inflammation, and not infection. Injury, in the absence of infection, and fresh calving, can also increase the SCC value in the milk. The SCC level may be confounded by high levels of a pathogen, including bacteria, yeast and fungi, each of which is a causative agent in mastitis. There are a number of limitations of the SCC type assay. Due to turbidity, milk cell counts cannot be made, and instead the samples are tested at remote laboratories using independent measurements. The time lapse between the collection of a milk sample and the transmittal of the cell count (SCC) information to the dairy farmer can exceed one month. This extraordinary delay in providing key information to the field agent or dairy farmer severely limits prompt action that might otherwise curtail the transmission of infection to unaffected animals. High level of SCC in the bulk tank deteriorates milk quality, and garners a lower price for the farmer. Furthermore, mastitis reduces milk output in the affected animal, and increases the likelihood of more frequent infections. Significantly, infected animals are only treated for a fixed term with antibiotics, and SCC levels are not typically monitored to confirm successful outcome. Consequently, an animal might be treated excessively, or not sufficiently. In the latter case, animals that respond poorly, or slowly to the antibiotic regimen, are likely to become chronic offenders that become drug resistant, yield poor quality of milk, incur large veterinarian expenses, eventually leading to the culling of the animal.

Federal and State guidelines allow up to ~$7.5 \times 10^5$ somatic cells/ml of raw milk. This is the upper limit, and milk quality is negatively affected at such high SCC levels. Typical values in the bulk tank may range from $2\text{-}4 \times 10^5$ SCC. The level permitted by the European dairy industry is more stringent ($4 \times 10^5$ somatic cells/ml).

There are currently two broadly available mastitis tests for monitoring milk quality. One assay, called the "Somatic Cell Count" (SCC) determines the level of somatic cells in the milk. The weaknesses of the SCC assay include the following. i) Inaccuracy, since it is negatively influenced by the presence of pathogens (the primary cause of mastitis), and necrotic tissue and blood in the milk. Moreover, clotting of the milk also interferes with this measurement. ii) The SCC assay is insensitive, and only provides a threshold value of the levels of somatic cells.

iii) The SCC does not provide early-diagnostic information, because the results are provided to the farm up to a month after the initial acquisition of milk samples. iv) An infected animal is typically not identified because SCC levels are generally measured in the bulk milk reservoir, which can contain milk from 50-100 cows. v) Because the SCC is measured in the bulk reservoir, a high somatic cell count would be caused by a very high level infection in a single individual cow. However, this compromises the quality of milk in the bulk reservoir and delays detection of the affected animal. Moreover, advanced mastitis necessitates more aggressive treatment, prolonged withdrawal of the animal from the milk line, and a higher probability of generating a chronically affected individual, all of which represent significant economic liabilities to the farm. vi) The SCC assay is hindered by the expense and delay of testing samples at a remote laboratory. Significantly, the delay prevents the implementation of prompt remedial action. Generally the farmer/field agent recognizes symptoms in an affected animal and removes it from the milk line. However, this represents an action after the infection has occurred. vii) Injury can also cause inflammation and high SCC levels. However, the milk quality might be unaffected since there is no infection. However, the dairyman might begin an antibiotic treatment regimen as a precaution, which would be undesirable.

The second assay is termed the "California Mastitis Test" (CMT). In this method milk from each quadrant of the udder is deposited into each of four shallow receptacles, to which a proprietary solution is added. Gentle mixing results in clumping of mastitis-positive samples. This is an imprecise assay that does not give any quantitative measurement of the level of infection. Moreover, the assay is quite insensitive, and does not detect lower levels of persistent mastitis.

Mastitis may be characterized as clinical or pre-clinical mastitis. Sub-clinical mastitis is not visually detected (redness, soreness and swelling of teats and udder), and milk quality is not severely diminished. However, some changes may be observed, including clots and runny consistency of the milk. Redness, soreness and swelling of the teats are occasionally observed. Clinical mastitis can be mild or severe, and is reflected by the level of SCC in the milk. A heavily infected animal will display significant redness, soreness, and a hard teat, which will necessitate antibiotic treatment. The onset of mastitis can be rapid, and cause impaired breathing, failure to eat, and significantly increased body temperature. A systemic infection is considered grave, and the animal is removed from the milk line, and treated with antibiotics for ~3 days. The specific duration of the treatment, and the number of days the cow is withheld from the milk line is defined by the manufacturer of the antibiotic. Following the treatment, the animal is kept off the milk line until antibiotic levels in the milk are reduced. Some animals may tolerate chronic sub-clinical mastitis, although the extent of this occurrence and its effect of milk output and quality have not been carefully determined, because there is no straightforward way to measure it. This Invention will easily detect the early stage of infection, and will permit prompt removal of affected individuals before the bulk reservoir is affected. Because chronically affected individually oscillate between high baseline of sub-clinical infection and full-blown infection, these candidates require constant monitoring, which is not possible with current methods, but can be easily achieved with the Invention described here.

Clinical mastitis causes greater than $ 4 billion in directly attributable losses for the dairy industry. However, this is an underestimate, because the financial loss caused by low quality milk and poor yield from sub-clinical cows, treatment of affected animals, withdrawal from the milk line, and occasional culling of ill animals is not estimated.

There is a need for improved methods and systems for detecting mastitis and assessing milk quality.

SUMMARY OF THE INVENTION

Methods for determining if one or more animals has mastitis are provided. In some embodiments, a test assay is performed to determine the level of proteasomes present in test sample of milk. The level of proteasomes present in the test sample is compared with a standard level of proteasomes in a control sample of milk from an uninfected animal and/or a control sample of milk from an animal with pre-clinical mastitis and/or a control sample of milk from an animal with clinical mastitis. The level of proteasomes present in the test sample relative to the standard level of proteasomes indicates the condition of the animal. Several embodiments involve measuring proteasome enzyme activity. Substrates are contacted with samples of milk and the level of processing of the substrate indicates the level of proteasomes. Several embodiments involve measuring the quantity of proteasomes, proteasome proteins, proteasome bound and regulating proteins and ubiquinated proteins. Several embodiments involve measuring the quantity of mRNA encoding proteasomes, proteasome proteins, and proteasome bound and regulating proteins.

Systems are also provided for detecting proteasome enzyme activity in a sample of fluid or the quantity of proteasomes, proteasome proteins, proteasome bound and regulating proteins, or mRNA encoding such proteins or of ubiquinated proteins. The systems generally comprise a device for measuring detectable signals; a sample container which can be received by the device to measure detectable signals in the sample container, and reagents used to carry out the test assay.

Sample containers are disclosed which comprise reagents used to carry out the test assay are disclosed. In some embodiments, the reagents may be disposed on an inner wall of the container. In some embodiments, the container or its cap is destroyed uoin use.

Methods for determining milk quality are also provided.

BRIEF DESCRIPTION OF THE FIGURES

FIG. 6 shows a list of antibodies to 19S regulator of ATPase.

DETAILED DESCRIPTION OF PREFERRED EMBODIMENTS

Definitions

Figure 1:
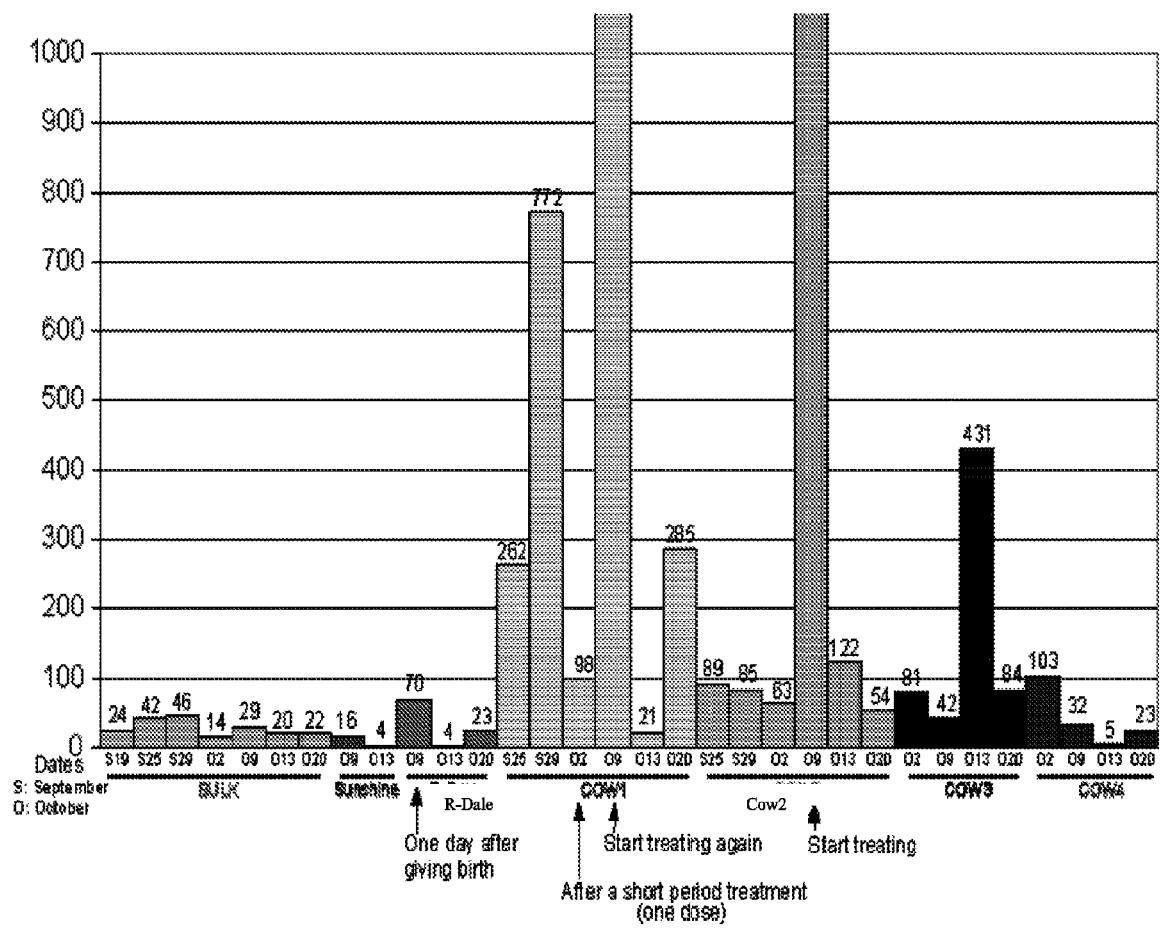
FIG. 1 shows the fold increase in proteasome activity in affected cow milk, as compared to normal healthy cow milk.

As used herein the term "level of proteasomes present" is meant to refer to the quantity of proteasomes present. The proteasomes may be from the animals somatic cells or from a bacteria, fungus and/or yeast organism infecting the animal. The level of proteasomes may be determined by direct quantification or by determining the level of proteasome enzyme activity or activity of enzymes associated with proteasome.

As used herein the term "standard level of proteasomes in a control sample of milk from an uninfected animal" is meant to refer to a typical quantity or range of quantities of proteasomes found in a sample of milk from an uninfected animal, wherein the sample is of a known sample volume, preferably the same volume as being used in a test assay.

As used herein, the term "proteasome enzyme activity" is meant to refer to enzymatic activity by one of the several proteasome enzymes present as part of the proteasome complex whereby a substrate is processed by the enzyme into one or more products which are distinguishable from the substrate. Proteasome enzymes include the chymotrypsin-like or chymotryptic protease, the trypsin-like or tryptic protease and the caspase like or post-acidic protease.

As used herein, the term "level of conversion of a proteasome enzyme substrate to a product" is meant to refer to the quantity of substrate converted to a product by an enzyme in a test period.

As used herein, the terms "trypsin-like substrate" and "tryptic substrate" are used interchangeable and meant to refer to substrates which can be spontaneously processed by the trypsin-like protease which is also referred to as tryptic protease.

As used herein, the terms "chymotrypsin-like substrate" and "chymotryptic substrate" are used interchangeable and meant to refer to substrates which can be spontaneously processed by the chymotrypsin-like protease which is also referred to as chymotryptic protease.

As used herein, the terms "caspase-like substrate" and "post-acidic protease substrate" are used interchangeable and meant to refer to substrates which can be spontaneously processed by the caspase-like protease which is also referred to as post-acidic protease.

As used herein, the term "ATPase subunit" is meant to refer to proteasome subunits which can hydrolyze ATP.

As used herein, the term "de-ubiquitinating substrate" is meant to refer to substrates which can be processed by the proteasome de-ubiquitinating enzyme.

Overview

The Ub/proteasome proteolytic pathway is required for efficient cell-cycle control, stress response, DNA repair, and differentiation (Glickman and Ciechanover (2002) *Physiol. Rev.* 82:373-428; Pickart (1997) *FASEB J.* 11:1055-1066; Varshaysky (1997) *Trends Biochem. Sci.* 22:383-387). Mutations in this pathway can cause pleiotropic defects because of its involvement in virtually all aspects of cell function.

Consequently, the characterization of the Ub/proteasome pathway for the development of treatment for cancer and other malignancies is an area of active investigation (Voorhees, et al. (2003) *Clin. Cancer Res.* 9:6316-6325; Yang, et al. (2004) *Clin. Cancer Res.* 10:2570-7; Yang, et al. (2004) *Clin. Cancer Res.* 10:2220-2221; Rossi and Loda (2003) *Breast Cancer Res.* 5:16-22; Ohta and Fukuda (2004) *Oncogene* 23:2079-2088).

The 26S proteasome is composed of a catalytic (20S) particle and a regulatory (19S) particle. The structure and function of the 20S catalytic particle is conserved in evolution, and its compartmentalized organization ensures that the proteolytic activities are sequestered within the interior of the proteasome (Baumeister, et al. (1998) *Cell* 25 92:367-380). The large 19S regulatory particle interacts with the 20S particle to facilitate recognition, unfolding and degradation of ubiquitinated substrates (Glickman, et al. (1998) *Mol. Cell. Biol.* 18:3149-3162; Groll, et al. (2000) *Nat. Struct. Biol.* 7:1062-1067). Ubiquitin (Ub) is covalently attached to lysine side-chains in cellular proteins (Pickart (2000) *Trends Biochem. Sci.* 25:544-548). The ligation of Ub to proteins requires the action of three enzymes termed Ub-activating (E1), Ub-conjugating (E2), and Ub-ligases (E3) (Glickman and Ciechanover (2002) supra). The sequential addition of Ub moieties results in the formation of a multi-Ub chain, which facilitates protein degradation by promoting translocation of substrates to the proteasome (Gregori, et al. (1990) *J. Biol. Chem.* 265:8354-8357; Thrower, et al. (2000) *EMBO J.* 19:94-102).

Malignant conditions are frequently associated with altered abundance and stability of regulatory proteins. It is therefore likely that the expression of a unique repertoire of proteins underlies the transition from normal to abnormal growth. Proteasome activity has been found to be elevated in esophageal cancer and cancer cachexia (Wyke, et al. (2004) *Br. J. Cancer* 91:1742-1750; Zhang, et al. (2004) *World J. Gastroenterol.* 10:2779-2784).

It has been shown that the co-translational degradation of newly synthesized misfolded proteins requires the Ub/proteasome system (Schubert, et al. (2000) *Nature* 404:770-774; Reits, et al. (2000) *Nature* 404:774-778; Turner and Varshaysky (2000) *Science* 289:2117-2220). Moreover, translation elongation factor 1-alpha (eEF1A) is required for the efficient degradation of nascent polypeptide chains, especially in ATP-depleting conditions, and in the presence of protein synthesis inhibitors (Chuang, et al. (2005) *Mol. Cell. Biol.* 25:403-413). eEF1A expression is increased in certain cancers, e.g., T-lymphoblastic cancer (Lamberti, et al. (2004) *Amino Acids* 26:443-448; Dapas, et al. (2003) *Eur. J. Biochem.* 270:3251-3262), a result that reflects a more general response to aberrant growth (Ejiri (2002) *Biosci. Biotechnol. Biochem.* 66:1-21).

The detection of proteasomes in milk may be used as an indicator of mastitis in a milk producing animal as well as a measure useful to assess the quality of the milk. Proteasomes are found in the somatic cells found in milk including the immune cells such as leukocytes which are present in increasing numbers as the level of infection progresses, as an animal goes from uninfected to severe mastitis. Additionally, the infectious organism responsible for mastitis also has proteasomes which can also be detected using distinct proteasome assays and antibodies.

Proteasomes are very robust by their nature and remain enzymatically active in milk. Thus, measuring the level of enzyme activity in a sample as compared to standard levels or ranges typical of uninfected, preclinical-mastitis, mild clinical mastitis, severe clinical mastitis and the like indicates not only a diagnosis of mastitis but also the severity of the condition. Proteasome enzyme activity assays are fast and simple and can be carried out with very little equipment or expense at the site where the milk is collected. When used in the context of dairy livestock, management and treatment of animals can be undertaken to maximize yield, minimize time off the line, and to improve the overall health and well being of the animals through early diagnosis and monitoring during treatment.

Likewise, because proteasomes are present in milk, they provide a useful target for detection by immunoassay, or as targets for detection of mRNA encoding proteasome protein components. In the case of immunoassay, the level of proteasome protein in a sample may be compared to standard levels or ranges typical of uninfected, preclinical-mastitis, mild clinical mastitis, severe clinical mastitis and the like to diagnosis mastitis and assess its severity. Similarly, the level of mRNA that encodes a proteasome protein in a sample may be quantified and compared to standard levels or ranges typical of uninfected, preclinical-mastitis, mild clinical mastitis, severe clinical mastitis and the like to diagnosis mastitis and assess its severity. These methods may be used to improve the productivity and health of animals.

Other methods of detecting proteasome levels include, for example, detection of levels of proteasome bound factors or mRNA encoding the same, detection of levels of proteasome regulatory factors or mRNA encoding the same, and levels based on interaction with organic copper complexes.

Enzyme Activity Assays

The proteasome contains three enzyme activities: 1) protease activity, 2) ATPase activity and 3) de-ubiquitination activity. Three different proteases perform the protease activity: 1) the trypsin-like enzyme, 2) the chymotrypsin like enzyme, and 3) the caspase-like enzyme. Each of these enzymes cleaves peptide bonds at the C terminus of different types of amino acids.

In each enzyme assay, the level of enzyme activity is determined by measuring the processing by the enzyme of a substrate into products. Typically, enzyme assays utilize labeled substrate in which the label become detectable after processing. In such case, the level of activity is indicated by measuring the amount of product produced. It is also possible to measure enzyme activity by using a labeled substrate in which the label is detectable when the substrate is unprocessed and becomes undetectable after processing. In such case, the level of activity is indicated by measuring the amount of substrate processed.

Protease Assays

As noted above, there are three different proteases, the trypsin-like enzyme, the chymotrypsin like enzyme, and the caspase-like enzyme, and each cleaves peptide bonds at the C terminus of different types of amino acids. In its usual functioning in the cells, proteins are labeled for destruction by attachment to ubiquitin and delivered to the proteasome where the proteins are de-ubiquitinated and unfolded so that they can be moved into the proteasome and processed by the proteases. The three proteases of the proteasome are located internally in a proteasome structure and so the proteins to be cleaved are unfolded and translocated into the proteasome. The proteases recognize and cleave by hydrolysis peptide bonds which are at the C terminus of different amino acid residues. The trypsin-like enzyme cleaves after a basic amino acid residue. The chymotrypsin like enzyme cleaves after a hydrophobic amino acid residue. The caspase-like enzyme cleaves after an acidic amino acid residue. Dick, T P et al. J. Biol. Chem. Vol 273 1998 provides a detailed analysis of the amino acid sequence preferred by the hydrolytic activities present in the proteasome.

In assays provided herein, substrates are used that are spontaneously processed by the proteasomes. Specifically, these substrates do not need to be attached to ubiquitin, or unfolded. To be spontaneously processed by a protease, the substrate must be of a size that it can enter the proteasome without the need for delivery proteins, de-ubiquitination, or unfolding. Thus, substrates that can be spontaneously processed are typically no longer in length than the length of a 3-6 amino acid peptide, and are no more than 13 Angstroms cross-wise so that it can freely enter the proteasome. The Structure of the 20S proteasome from yeast at 2.4 Å resolution is reported in Groll, M et al. Nature 386, 463-471 (3 Apr. 1997). The crystal structure of the 20S proteasome from the yeast *Saccharomyces cerevisiae* was reported to show that its 28 protein subunits are arranged as a complex in four stacked rings and occupy unique locations. The interior of the particle, which harbors the active sites of the three proteases, is only accessible by two 13 Angstrom diameter axial pores.

To be processed, the substrate must comprise a peptide bond at the C terminus of an amino acid residue. Accordingly, the general formulae for the substrates are X—Y-A=Z for trypsin-like substrate, X—Y—B=Z for chymotrypsin-like substrate and X—Y—C=Z for caspase-like substrate, wherein X is a blocking moiety which prevents N terminal proteases from processing the substrate, Y is absent or moiety which links X to A, A is a basic amino acid or moiety which forms a peptide bond with Z that is recognized and cleaved by the trypsin-like protease, B is a hydrophobic amino acid or moiety which forms a peptide bond with Z that is recognized and cleaved by the chymotrypsin-like protease, C is an acidic amino acid or moiety which forms a peptide bond with Z that is recognized and cleaved by the caspase-like protease, = is a peptide bond that links A, B or C to Z and that is recognized and cleaved by the protease, and Z is a label that is either undetectable when linked to A, B or C and becomes detectable when = is hydrolyzed, or is detectable when linked to A, B or C and becomes undetectable when = is hydrolyzed.

Typically, the substrates are N-terminally blocked linear peptides that are not folded and have a secondary structure and linked at their C terminus to detectable labels by a peptide bond. Thus, according to the formulae above, the peptides are Y-A, Y—B or Y—C in which Y is 1-4 amino acids, A is an amino acid which is recognized by trypsin-like protease, B is an amino acid which is recognized by chymotrypsin-like protease, and C is an amino acid which is recognized by caspase-like protease.

N terminal blocking moieties are well known. Examples of N terminal blocking moieties include succinimide (Suc), (Boc), benzyloxycarbonyl (Z) and benzoyl (Bz).

Examples of amino acids recognized by trypsin-like protease, i.e. A amino acids, include the basic amino acids Arginine; Lysine; in some cases Histidine.

Examples of amino acids recognized by chymotrypsin-like protease, i.e. B amino acids, include the hydrophobic amino acids Tryptophan; Tyrosine; Phenylalanine; Methionine; Leucine; and Isoleucine.

Examples of amino acids recognized by caspase-like protease, i.e. C amino acids, include the acidic amino acids Glutamic acid and Aspartic acid.

Detectable labels useful in the methods are well known. Examples of detectable labels include fluorescent and luminescent labels. Fluorescent, luminescent and colorimetric labels and methods of detecting and measuring quantities with them are well known and readily understood.

Examples of fluorescent labels include 7-amino-4-methylcoumarylamide (AMC).

Examples of luminescent labels include luciferin.

Examples of colorimetric labels include copper complex reagents.

Examples of trypsin-like substrates include Ac-Arg-Leu-Arg-AMC;

Boc-Leu-Arg-Arg-AMC; Bz-Val-Gly-Arg-AMC. In some embodiments the substrate comprises the amino acid sequence as one of these substrates but a different blocking moiety and or label.

Examples of chymotrypsin-like substrates include Suc-Arg-Pro-Phe-His-Leu-Leu-Val-Tyr-AMC (SEQ ID NO:1); Z-Gly-Gly-Leu-βNA; Z-Gly-Gly-Leu-AMC; Suc-Leu-Leu-Val-Tyr-AMC (SEQ ID NO:2); Suc-Leu-Tyr-AMC. In some embodiments the substrate comprises the amino acid sequence as one of these substrates but a different blocking moiety and or label.

Examples of caspase-like substrates include Ac-Gly-Pro-Leu-Glu-AMC (SEQ ID NO:3); Z-Leu-Leu-Asp-AMC; Z-Leu-Leu-Asp-βNA; Ac-nLeu-Pro-nLeu-Glu-AMC (SEQ ID NO:4). In some embodiments the substrate comprises the amino acid sequence as one of these substrates but a different blocking moiety and or label.

Fluoresence may be measured using standard commercially available fluorometer equipment. Examples of fluorescence detectors include Turner 7000 (Sunnyvale Calif.), Turner Aquafluor™ (Sunnyvale Calif.), and TECAN Geneosis plate reader.

The hydrolysis of test substrates by chymotryptic, tryptic and post-acidic proteases is well described in the literature. These substrates are typically small peptide derivatives that are linked to a fluorogenic reagent that upon release by cleavage by a proteasome protease can be excited by near-UV light to generate a highly sensitive and specific fluorescent signal. The structure, sequence, hydrophobicity and other biophysical properties of these synthetic substrates have been described, and the compounds that are commercially available represent versions that can be generated in bulk and yield good signal.

Sato, S et al. (1991) Eye Res. 10, 485-489 refer to the use of labeled diisopropyl fluorophosphates to measure chymotrypsin-like activity. The degradation of beta-galactosidase based substrates can be monitored using labeled proteins, and by measuring enzymatic activity using ONPG (o-Nitrophenyl-beta-galactopyranoside) or CPRG (chlorophenol red-beta-D-galactopyranoside). A plating and chromogenic assay can also be performed using IPTG (isopropyl beta-D-thiogalactopyranoside) and X-gal (5-bromo-4-chloro-3-indolyl-beta-D-galactopyranoside). Other enzymes have also been developed into proteasome substrates (including glucuronidase, DHFR, GST and GFP).

Andreas Bachmair and Alexander Varshaysky 1989 Cell, Vol 56, 1019-1032 report that the degradation of DHFR and beta-galactosidase type substrates will show a loss of signal, in the presence of productive degradation by the proteasome. In contrast, degradation of fluorogenic peptide substrates yields a time-dependent increase in fluorescence signal, as the substrate is hydrolyzed by the proteasome.

In some embodiments, a test sample is added to a container such as a cuvette or test tube. Generally, 0.5-2 ml, typically 1 ml samples are tested. In some embodiments, the container is preloaded with substrate. In some embodiments, the container is preloaded with substrate that is dried and adhered to an inner surface of the container. In some embodiments, the container comprises a cap with a reservoir that comprises substrate. After adding the milk, the cap is used to close the container upon depressing it, the substrate is displaced from the reservoir into the container, typically by rupturing the reservoir. In some embodiments, the substrate is provided in a container such as a dropper or metered dispensers and the substrate is added to the container. The test sample may be mixed and maintained for a period of time sufficient to allow detection of an amount of detectable label that corresponds to the assessment standard being used. Generally, the time of the reaction is 30 seconds to about 5 minutes. After sufficient time has elapsed, if the detectable label is a fluorescent label, the container may be inserted in the fluorometer or luminometer, and the level of fluorescence or luminescence detected. After sufficient time has elapsed, if the detectable label is a luminescent label, the light emitted from the container may be measured and the level of luminescence detected. After sufficient time has elapsed, if the detectable label is a colorimetric label, the container may be inserted in the colorimeter and the level of light of a predetermined wavelength is detected or, if the change in color can be detected visually in the presence of a level of proteasomes indicative of some level of infection, the visual inspection of the container may be undertaken to determine the results. In each case, the results may be compared to standards known to correspond to one or more levels of infection.

In some embodiments, a test sample is contacted with a solid surface, such as a stick of plastic or paper. In some embodiments, the solid surface is preloaded with substrate such that contacting the test sample with the solid surface places the test sample in contact with the substrate disposed thereon. Alternatively, for example, substrate is contacted with the solid surface after or with the test sample so that the sample is mixed with the substrate. The solid surface with the test sample is maintained for a specified period of time sufficient to allow enzyme present in the sample to process the substrate and produce a detectable label that manifests itself as a color change on the solid surface. The color of the solid surface may be compared to a standard color chart that includes the colors for one or more levels of proteasomes corresponding to one or more levels of infection. Alternatively, the amount of substrate on the surface may be measured with sufficient precision such that when contacted for a specified period of time with a sample containing proteasomes above a threshold amount that corresponds to a level of infection, the solid surface changes color such that it can be visually detected. That is, the amount of reagent disposed on a test strip is calibrated so that a detectable reaction only occurs if the amount of enzyme present is greater than a threshold level. Thus, a test strip is contacted with a milk sample for a specified time and if it undergoes a detectable reaction in that time period, such as changing color, the assay indicates protease levels above a known threshold. For example, the test strip may be manufactured so that it will only change color after a specified time if the protease levels are consistent with a pre-clinical mastitis level, or clinical mastitis level.

ATPase Assay

The intact 26S proteasome contains two 19S regulatory particles. Each 19S particle contains a ring of six ATPases. Therefore, an intact 26S proteasome will contain 12 ATP hydrolyzing enzymes. Consequently, purified proteasomes have robust ATPase activity that can be measured by a broad range of assays that are well known and routinely performed by those skilled in the art. The luciferase-based ATPase activity is one of the most sensitive. In some embodiments, the assay determines ATP hydrolyzing activities present in raw milk. In some embodiments, the assay comprises first isolate proteasomes from a sample and then measuring proteasome-specific ATPase activity. Proteasome isolation may be accomplished, for example, by the method that is disclosed in U.S. Pat. No. 6,294,363, which is incorporated herein by reference. Typical detection methods include a luciferase/luciferin based approach which generates a robust luminescent signal of high specificity, and very broad dynamic range (linearity over 5-orders of magnitude) however, other systems using different types of detectable signals may also be routine performed. These methods provide another way to monitor proteasome abundance and activity. DeMartino, G. N et al. Vol. 269, No. 33, Issue of August 19, pp. 20878-20884, 1994 reports that PA700, an ATP-dependent activator of the 20 S proteasome, is an ATPase containing multiple members of a nucleotide-binding protein family De-Ubiquitization Assay Ubiquitination, the conjugation of proteins to ubiquitin that occurs in a number of cellular processes including endocytosis, DNA repair and degradation by the 26S proteasome. is reversible as a number of deubiquitinating enzymes mediate the disassembly of ubiquitin-protein conjugates. Some deubiquitinating enzymes are associated with the 26S proteasome contributing to and regulating the particle's activity. At least three different deubiquitinating enzymes have been detected in proteasomes.

Proteasome activity can be measured by monitoring associated de-ubiquitinating activity. The vast majority of substrates that are degraded by the proteasome are attached to a chain of ubiquitins. However, these ubiquitins are not degraded along with the substrate, but are released, recycled and used again to target additional proteins to the proteasome. Significantly, the de-ubiquitination of the substrate is required for successful degradation.

Deubiquitinating activity can be measured using well known routine assays and commercially available fluorogenic substrates (such as for example Arg-Gly-Gly-AMC). The method to measure proteasome-associated de-ubiquitination involves the addition of a substrate such as for example Ubiquitin-AMC or Arginine-Glycine-Glycine-AMC to a reaction that contains the de-ubiquitinating activity. Cleavage of the AMC from the ubiquitin, or from the peptide (RGG-AMC) generates a highly specific fluorescent signal that can be readily detected with a fluorometer. The sequence of the peptide RGG is optimized, although other derivatives will also work. Therefore, the key aspect is that measurement of de-ubiquitinating activity of the proteasome (irrespective of the substrate used), provides an alternate way to measure the level of proteasome and proteasome activity.

Stone, M et al. J Mol. Biol. 2004 Nov. 26; 344(3):697-706 refer to Uch2/Uch37 as the major deubiquitinating enzyme associated with the 26S proteasome in fission yeast. Fission yeast Uch2 and Ubp6, two proteasome associated deubiquitinating enzymes is reported to be characterized. The human orthologues of these enzymes are known as Uch37 and Usp14, respectively. The subunit Uch2/Uch37 is reported to be the major deubiquitinating enzyme associated with the fission yeast 26S proteasome while the activity of Ubp6 appears to play a more regulatory and/or structural role involving the proteasome subunits Mts1/Rpn9, Mts2/Rpt2 and Mts3/Rpn12. Ubp6 is reported to become essential when activity of these subunits is compromised by conditional mutations.

Immunoassay

A simple way to gauge the level of the proteasome is by using immunologic methods. Both monoclonal and polyclonal antibodies are available to all subunits of the proteasome. Antibodies against human proteasome subunits can cross-react against the bovine counterparts. The intact 26S proteasome contains ~32 subunits, while the immunoproteasome contains ~16 subunits. A collection of antibodies that are purchased or generated can be used to monitor proteasome abundance. Methods of immuno-detection include ELISA, immunoblotting, and antibody-based interference assays. Antibodies conjugated to biotin, magnetic beads, enzymes (such as alkaline phosphatase) represent other ways to monitor the levels of proteasome subunits.

Kopp, F et al. PNAS Apr. 1, 1997 vol. 94 no. 7 2939-2944 refer to subunit arrangement in the human 20S proteasome and report that in human 20S proteasomes two copies of each of seven different α-type and seven different β-type subunits are assembled to form a stack of four seven-membered rings, giving the general structure α1-7, β1-7, β1-7, α1-7. By means of immunoelectron microscopy and chemical crosslinking of neighboring subunits, the positions of the individual subunits in the proteasome were determined. The topography shows that for the trypsin-like, the chymotrypsin-like, and the post-glutamyl cleaving activities, the pairs of β type subunits, which are thought to form active sites, are nearest neighbors.

Tanaka K. and C. Tsurumi Mol Biol Reports 24:(1-2)3-11 Mar. 1997 refer to the subunits and functions of the 26S proteasome and report that the 26S proteasome is an eukaryotic ATP-dependent, dumbbell-shaped protease complex with a molecular mass of approximately 2000 kDa. It consists of a central 20S proteasome, functioning as a catalytic machine, and two large V-shaped terminal modules, having possible regulatory roles, composed of multiple subunits of 25-110 kDa attached to the central portion in opposite orientations. The regulatory subunits are classified into two subgroups, a subgroup of at least 6 ATPases that constitute a unique multi-gene family encoding homologous polypeptides conserved during evolution and a subgroup of approximately 15 non-ATPase subunits, most of which are structurally unrelated to each other.

Coret J, Heinemeyer, W et al. Biochemistry 1994, 33, 12229-1 2237 12229, refer to PRES and PRE6, as genes encoding 20s proteasome subunits from Yeast and report that the 20s proteasome of eukaryotes is an abundant multicatalytic/multifunctional proteinase complex composed of an array of nonidentical subunits which are encoded by a- or 0-type members of the proteasomal gene family. In budding yeast, 14 subunits had been detected but ony 12 proteasomal genes had been cloned. The authors cloned two additional proteasomal genes, PRE5 and PRE6, which both encode essential α-type subunits. Sequence comparison of all known eukaryotic proteasomal proteins show the presence of a total of 14 subgroups, which can be divided into seven a- and seven 0-type groups. Including the Pre5 and Pre6 proteins, every subgroup contains a single yeast member.

Diagnostic marker proteins in a sample of raw milk can be detected via binding assays, wherein a binding moiety which specifically recognizes the marker protein (for instance an antibody or naturally occurring binding partner), is introduced into a sample suspected of containing the marker protein. In such an assay, the binding partner is generally labeled as, for example, with a radioisotopic or fluorescent marker. Labeled antibodies can be used in a similar manner in order to isolate selected marker proteins.

Using the instant marker proteins or antibodies, the skilled artisan can use any one of a variety of detection methods for detecting mastitis. The methods typically employ the steps of detecting, by some means, the level of one or more Ub/proteasome pathway marker protein in a sample and comparing said level to that of the marker protein in a control sample to determine whether there is a detectable increase (e.g., 1.5-fold or more) in the level of the marker protein. In general, the test sample can be obtained from young healthy cows, and confirmed independently using SCC analysis.

In a protein-based assay, the marker protein in a sample is detected, for example, by combining the marker protein with an antibody-based binding moiety capable of specifically binding the marker protein. An antibody-based binding moiety of the present invention is intended to include an antibody, antibody fragment or antibody derivative. Binding proteins can also be designed which have enhanced affinity for a target protein. Optionally, the binding moiety can be linked with a detectable label, such as an enzymatic, fluorescent, radioactive, phosphorescent or colored particle label. The labeled complex is detected, e.g., visually or with the aid of a spectrophotometer or other detector.

A Ub/proteasome pathway or ancillary marker protein can also be detected using any of a wide range of immunoassay techniques with qualitative or quantitative results. For example, the skilled artisan can employ the sandwich immunoassay format to detect mastitis in a milk sample. Alternatively, the skilled artisan can use conventional immuno-histochemical procedures for detecting the presence of the proteasome or ancillary protein using one or more labeled binding moieties. It is contemplated that either an absolute, semi-quantitative, or relative level of protein expression can be detected using the immunoassays disclosed herein.

In a sandwich immunoassay, two antibodies capable of binding the marker protein generally is used, e.g., one immobilized onto a solid support and one free in solution and labeled with a detectable chemical compound. Examples of chemical labels that are useful for the second antibody include radioisotopes, fluorescent compounds, and enzymes or other molecules that generate colored or electrochemically active products when exposed to a reactant or enzyme substrate. When a sample containing the marker protein is placed in this system, the marker protein binds to both the immobilized antibody and the labeled antibody, to form a "sandwich" immune complex on the support's surface. The complexed protein is detected by washing away non-bound sample components and excess labeled antibody, and measuring the amount of labeled antibody complexed to protein on the support's surface. Alternatively, the antibody free in solution can be detected by a third antibody labeled with a detectable moiety which binds the free antibody or, for example, a hapten coupled thereto.

Both the sandwich immunoassay and tissue immunohistochemical procedures are highly specific and very sensitive, provided that labels with good limits of detection are used. A detailed review of immunological assay design, theory and protocols can be found in numerous texts in the art, including *Practical Immunology*, Butt, W. R., ed., (1984) Marcel Dekker, New York; and *Antibodies, A Laboratory Approach*, Harlow, et al., eds. (1988) Cold Spring Harbor Laboratory.

In general, immunoassay design considerations include preparation of antibodies (e.g., monoclonal or polyclonal antibodies), antibody fragments, or antibody derivatives having sufficiently high binding specificity for the target protein to form a complex that can be distinguished reliably from products of nonspecific interactions. As used herein, the term "antibody" is understood to mean binding proteins, for example, antibodies or other proteins comprising an immunoglobulin variable region-like binding domain, having the appropriate binding affinities and specificities for the target protein. Higher antibody binding specificity will permit detection of lower amounts of the target protein. As used herein, the terms "specific binding" or "specifically binds" are understood to mean that the binding moiety, for example, an antibody, has a binding affinity for the target protein of greater than $10^5$ $M^{-1}$ or greater than about $10^7$ $M^{-1}$.

Antibody binding domains also can be produced biosynthetically and the amino acid sequence of the binding domain manipulated to enhance binding affinity with a preferred epitope on the target protein. Specific antibody methodologies are well-understood and described in the literature. A more detailed description of their preparation can be found, for example, in Practical Immunology (1984) supra.

Chimeric antibodies are also contemplated. Techniques developed for the production of chimeric antibodies (Morrison, et al. (1984) *Proc. Natl. Acad. Sci. USA* 81:6851-6855; Neuberger, et al. (1984) Nature 312:604-608; Takeda, et al. (1985) *Nature* 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region.

Antibodies can also be modified, e.g., to produce a number of well-characterized fragments generated by digestion with various peptidases. For example, pepsin digestion of an antibody produces F(ab)'$_2$. The F(ab)'$_2$ can further be reduced under mild conditions to break the disulfide linkage in the hinge region, thereby converting the F(ab)'$_2$ dimer into an Fab' monomer. The Fab' monomer is essentially a Fab with part of the hinge region (see, *Fundamental Immunology, Third Edition* (1993) W. E. Paul, ed., Raven Press, NY). While various antibody fragments are defined in terms of the digestion of an intact antibody, one of skill will appreciate that such fragments can be synthesized de novo either chemically or by utilizing recombinant DNA methodology. Accordingly, the term antibody fragment also includes fragments either produced by the modification of whole antibodies or those synthesized de novo using recombinant DNA methodologies. Thus, an antibody fragment includes, but is not limited to, single chain antibodies, Fab fragments, F(ab')$_2$ fragments, diabodies (Holliger, et al. (1993) *Proc. Natl. Acad. Sci. USA* 90:6444; Poljak (1994) *Structure* 2:1121-1123), fragments produced by a Fab expression library (Huse, et al. (1989) Science 246:1275-1281), and epitope-binding fragments of any of the above.

Antibody derivatives such as peptide aptamers, which are selected for specifically binding to a proteasome subunit or ancillary protein in mastitis, are also provided in the instant invention. Peptide aptamers can be rationally designed or screened for in a library of aptamers (e.g., provided by Aptanomics SA, Lyon, France). In general, peptide aptamers are synthetic recognition molecules whose design is based on the structure of antibodies. Peptide aptamers consist of a variable peptide loop attached at both ends to a protein scaffold. This double structural constraint greatly increases the binding affinity of the peptide aptamer to levels comparable to that of an antibody (nanomolar range).

Binding moieties to the instant protein markers are used in the diagnostic assays disclosed herein as well as in kits to detect the level of the proteins in a milk sample. For example, a kit of the invention can include one or more binding moieties (e.g., antibodies, antibody fragments, or antibody derivatives) which bind specifically to one or more Ub/proteasome pathway or ancillary proteins and which permit the relative level and/or specific concentration of the Ub/proteasome pathway or ancillary proteins to be detected and/or quantitated in a milk sample.

Suitable kits for detecting Ub/proteasome pathway or ancillary proteins are contemplated to include, e.g., a receptacle or other means for capturing a sample to be evaluated, and means for detecting the presence and/or quantity in the sample of one or more of the Ub/proteasome pathway or ancillary proteins described herein. As used herein, "means for detecting" in one embodiment includes one or more antibodies specific for these proteins and means for detecting the binding of the antibodies to these proteins by, e.g., a standard sandwich immunoassay as described herein. Where the presence of a protein within a cell is to be detected, e.g., as from a milk sample, the kit also includes a means for separating the proteasomes from fat globules and casein present in the milk. The kit can further contain written information, such as procedures for carrying out the method of the present invention or analytical information, such as representative values for proteasome activity as a function of SCC levels, as well as with low and high expression levels of a specific reference protein. Such a kit is developed, validated and commercially available. (See U.S. Pat. No. 6,294,363).

Antibodies against Ubiquitin and its derivatives also provide a method for monitoring the abundance of this pathway, since the majority of proteasome-substrates are attached to multi-ubiquitin chains. A kit to achieve this is developed, validated and commercially available. (See U.S. Published Application No. 20050287608). A ubiquitin binding matrix may be used to collect ubiquitinated proteins from raw milk. The level of such proteins may be measured and compared to the range found in milk from uninfected individuals.

Nucleic Acid Based Assay

In other embodiments, the occurrence of mastitis can also be determined by detecting, in a milk sample, one or more nucleic acid molecules encoding one or more Ub/proteasome pathway or ancillary proteins. Using methods well-known to those of ordinary skill in the art, one or more oligonucleotide probes are designed to specifically hybridize with a nucleic acid molecule encoding a Ub/proteasome pathway or ancillary protein, e.g., nucleic acid molecules disclosed in the GENBANK Accession Nos. disclosed herein.

The expression of proteasome subunits and proteasome-associated factors can be readily determined, in real time, using quantitative PCR. The sequence of the human genome is available, and the design of effective PCR oligonucleotides can be generated using both public and proprietary programming software. (Bovine-specific RNA sequences will be based on homology to other mammalian species, and further refined as nucleic acid sequences become available). The 26S proteasome contains ~32 distinct subunits, whose sequence is highly conserved across evolution. The immunoproteasome contains fewer than 32, but does contain ~5 novel subunits. Additionally, hundreds of regulatory factors form transient interactions with the proteasome. Antibodies against human, mouse, rat, dog, worm, fly, yeast and other species will be tested for cross-reactivity against the bovine proteins. In tests conducted thus far, all the human specific antibodies examined have reacted against the bovine proteins.

A target nucleic acid molecule encoding a Ub/proteasome pathway or ancillary protein marker can be detected using a labeled binding moiety capable of specifically binding the target nucleic acid. The binding moiety can be, for example, a protein, a nucleic acid or a peptide nucleic acid. Additionally, a target nucleic acid, such as an mRNA encoding a Ub/proteasome pathway or ancillary protein, can be detected by conducting, for example, a northern blot analysis using labeled oligonucleotides, e.g., nucleic acid fragments complementary to and capable of hybridizing specifically with at least a portion of a target nucleic acid.

More specifically, gene probes composed of complementary RNA or, preferably, DNA to the Ub/proteasome pathway or ancillary protein nucleotide sequences or mRNA sequences encoding Ub/proteasome pathway or ancillary proteins can be produced using established recombinant techniques or oligonucleotide synthesis. The probes hybridize with complementary nucleic acid sequences presented in the test specimen, and provide exquisite specificity. A short, well-defined probe, coding for a single unique sequence is most precise and preferred. Larger probes are generally less specific. While an oligonucleotide of any length can hybridize to an mRNA transcript, oligonucleotides typically within the range of 8-100 nucleotides, preferably within the range of 15-50 nucleotides, are envisioned to be most useful in standard hybridization assays. Choices of probe length and sequence allow one to choose the degree of specificity desired. Hybridization is generally carried out at from 50° C. to 65° C. in a high salt buffer solution, formamide or other agents to set the degree of complementarity required. Furthermore, the state of the art is such that probes can be manufactured to recognize essentially any DNA or RNA sequence. For additional methodologies, see, for example, *Guide to Molecular Techniques*, Berger, et al. (1987) Methods of Enzymology, Vol. 152. A wide variety of different labels coupled to the probes or antibodies can be employed in the instant assays. The labeled reagents can be provided in solution or coupled to an insoluble support, depending on the design of the assay. The various conjugates can be joined covalently or non-covalently, directly or indirectly. When bonded covalently, the particular linkage group will depend upon the nature of the two moieties to be bonded. A large number of linking groups and methods for linking are taught in the literature. Broadly, the labels can be divided into the following categories: chromogens; catalyzed reactions; chemiluminescence; radioactive labels; and colloidal-sized colored particles. The chromogens include compounds which absorb light in a distinctive range so that a color is observed, or emit light when irradiated with light of a particular wavelength or wavelength range, e.g., fluorescers. Both enzymatic and nonenzymatic catalysts can be employed. In choosing a proteasome substrate, there will be many considerations including the stability of the substrate. A chemiluminescent label involves a compound that becomes electronically excited by a chemical reaction and emits light that serves as a detectable signal or donates energy to a fluorescent acceptor. Radioactive labels include various radioisotopes found in common use such as the unstable forms of hydrogen, iodine, phosphorus, sulphur, or the like. Colloidal-sized colored particles involve material such as colloidal gold that, in aggregate, form a visually detectable distinctive spot corresponding to the site of a substance to be detected. Additional information on labeling technology is disclosed, for example, in U.S. Pat. No. 4,366,241.

Once the level or activity of Ub/proteasome pathway or ancillary protein or nucleic acid encoding such protein is detected or measured in the test milk sample, it is compared to the level or activity of Ub/proteasome pathway or ancillary protein or nucleic acid encoding such protein in one or more controls in order to determine whether the subject from which the sample was obtained has mastitis.

As exemplified herein, a control can be a milk sample obtained from a healthy cow. By using one or more control samples (e.g., in a panel), the skilled technician can compare the level of proteasome activity, or abundance of ancillary proteins in an immunological or immunohistochemical assay, or absolute level of expression in an ELISA for a semi-quantitative or quantitative result. Although the present methodology will emphasize the characterization of proteasome activity as a key measure of infection, we recognize that measuring the abundance of the proteasome and ancillary components, and/or the levels of specific mRNAs or DNA, will also serve as useful indicators of mastitis.

Interaction with Organic Copper Complexes

The abundance of the proteasome can be determined by examining its interaction with organic copper complexes (including NCI-109268 and bis-8-hydroxyquinoline copper(II) [Cu(8-OHQ)$_2$], and 5,7-dichloro-8-hydroxyquinoline-copper(II),). These reagents inhibit the chymotryptic activity of the proteasome, and generate a green stain upon interaction with the proteasome. The ability of specific proteasome subunits and/or regulatory factors to bind copper may be used in detection system to measure proteasome levels.

A variety of copper complexes can bind and inhibit the proteasome. Furthermore, the interaction results in a green stain that can be detected. Copper-binding compounds have been reported as proteasome inhibitors and apoptosis inducers in human cancer. Several copper-binding compounds have been reported to spontaneously complex with copper and form active proteasome inhibitors and apoptosis inducers. For example, compounds in the quinoline and dithiocarbamate families may bind with copper and inhibit the proteasome activity. Compounds, such as clioquinol and pyrrolidinedithiocarbamate as examples, form complexes with copper and bind to proteasomes.

Detection of Proteasome Regulatory Factors

The proteasome can be rapidly purified, for example, as disclosed above. U.S. Pat. No. 6,294,363 provides for one-step, rapid purification of proteasomes. The presence of key regulatory factors can be established using immunologic methods, such as antibodies. The presence of these factors in raw milk would provide a key indicator for the presence of proteasomes, and therefore a gauge of the level of inflammatory cells in the milk. As noted above, this provides a way to assess the level of infection, which is strongly related to the level of pathogen/infection.

Detection of Proteasome Bound Factors

An important, and additional application of this method relates to the fact that some proteasome-bound factors have well-described biochemical properties. We have shown previously that ubiquitin-conjugating enzymes (Ubc4, Ubc5), and translation elongation factor (eEF1A), can be detected in association with the proteasome. In addition, other reports have described the association of ubiquitin-E3 ligases (Ubr1, Scf), de-glycosylases (Png1) and kinases (Cdc2) with the proteasome. Proteasomes have also been reported to have RNAase activity. Notably, all these factors have well-described biochemical properties that can be readily measured. Therefore, measuring these and other biochemical activities in purified proteasomes provides a method for detecting the levels of proteasomes, and the likelihood of mastitis.

Gautier-Bert K, et al., Molecular Biology Reports Volume 30, Number 1, March 2003, refer to and report partially reconstituted 20S proteasome/RNA complexes using oligonucleotides corresponding to ARE (adenosine- and uridine-rich element) $(AUUUA)_4$ (SEQ ID NO:5) and HIV-TAR (human immunodeficiency virus-Tat transactivation response element), a stem-loop structure in the 5' UTR (untranslated region) of HIV-mRNAs. RNAs which associate with proteasomes are degraded by proteasomal endonuclease activity. The formation of these 20S proteasome/RNA substrate complexes is rather specific since 20S proteasomes do not interfere with truncated TAR that is not cleaved by proteasomal endonuclease. In addition, affinity of proteasomes for $(AUUUA)_4$ (SEQ ID NO:5) is much stronger than it is for HIV-TAR.

Jarrousse, Anne-Sophie et al. J Biol Chem, Vol. 274, Issue 9, 5925-5930, Feb. 26, 1999 refer to Possible Involvement of Proteasomes (Prosomes) in AUUUA-mediated mRNA Decay and reports on a cellular target for proteasomal endonuclease activity and indicate that 20S proteasomes interact with the 3'-untranslated region of certain cytoplasmic mRNAs in vivo, and 20S proteasomes isolated from Friend leukemia virus-infected mouse spleen cells were found to be associated with an mRNA fragment showing great homology to the 3'-untranslated region of tumor necrosis factor β mRNA that contains AUUUA sequences. Destabilization of oligoribonucleotides corresponding to the 3'-untranslated region of tumor necrosis factor β by 20 S proteasomes and the creation a specific cleavage pattern are reported. The cleavage reaction is accelerated with increasing number of AUUUA motifs, and major cleavage sites are localized at the 5' side of the A residues.

Detectably labeled RNA substrates may by used in assays to detect proteasome RNase activity in a milk sample. The level of RNase activity relative to the level of RNase activity in milk from an uninfected animal and/or infected animal may be indicates whether the animal is infected or not.

Proteasome associated Peptide N-glycanase (PNGase; glycoamidase; N-glycanase) activity may also be measured as an indication of proteasome levels. Png1 is a deglycosylating enzyme that can remove asparagine-linked (N-linked) glycans from glycoproteins/glycopeptides that have been targeted for degradation by the proteasome. The interaction between Png1 and the proteasome-docking (shuttle) factor Rad23 is significant, because this interaction promotes the localization of PNGase activity with the proteasome. Suzuki T, et al. FASEB J., 16, 635-641, 2002 2 refer to the occurrence, primary structure, and potential functions of cytoplasmic peptide:N-glycanase (PNGase) in eykaryotic cells. Suzuki T, and W J Lennarz Biochem. Biophys. Res. Commun, 302, 1-5, 2003 hypothesize that a glycoprotein-degradation complex is formed by protein-protein interaction involves cytoplasmic peptide:N-glycanase.

Assays measuring removal of asparagine-linked (N-linked) glycans from glycoprotein/glycopeptides substrates by Png1 may be useful in measuring proteasome levels in a sample. In such assays, the substrate comprises a detectable label that is either detectable before processing by Png1 but not after, or not detectable before processing by Png1 but detectable after the enzyme reaction.

Proteasome-associated lipase activity may also be used as an enzyme based assay which correlates to proteasome levels. Ohsak, Y et al. MBC, Vol. 17, Issue 6, 2674-2683, June 2006 (10.1091/mbc.E05-07-0659 on Apr. 5, 2006) refers to cytoplasmic lipid droplets as being sites of convergence of proteasomal and autophagic degradation of Apolipoprotein B. Lipid esters stored in cytoplasmic lipid droplets (CLDs) of hepatocytes are reported to be used to synthesize very low-density lipoproteins (VLDLs), into which apolipoprotein B (ApoB) is integrated cotranslationally. Using Huh7 cells derived from human hepatoma and competent for VLDL secretion, ApoB was found to be is highly concentrated around CLDs to make "ApoB-crescents." ApoB-crescents were reported seen in <10% of Huh7 cells under normal conditions, but the ratio increased to nearly 50% after 12 h of proteasomal inhibition by N-acetyl-L-leucinyl-L-leucinyl-L-norleucinal. Electron microscopy reportedly showed ApoB to be localized to a cluster of electron-lucent particles 50-100 nm in diameter adhering to CLDs. ApoB, proteasome subunits, and ubiquitinated proteins were detected in the CLD fraction, and this ApoB was ubiquitinated. Proteasome inhibition reportedly caused increases in autophagic vacuoles and ApoB in lysosomes in which ApoB-crescents began to decrease after 12-24 h of proteasomal inhibition, but the decrease was blocked by an autophagy inhibitor, 3-methyladenine Inhibition of autophagy alone reportedly caused an increase in ApoB-crescents. Proteasomal and autophagy/lysosomal degradation of ApoB may occur around CLDs and that the CLD surface functions as a unique platform for convergence of the two pathways.

Detectably labeled lipase substrates may be used to determine proteasome-associated lipase activity as an indication of proteasome levels in a sample. The reagents referred to herein may be adapted to detectably label lipase substrates. Enzyme activity may be measured and used as an indicator of proteasome levels.

Verma R, et al. Mol Biol Cell. 2000 October; 11(10):3425-39 refer to identification of nucleotide-sensitive proteasome-interacting proteins by mass spectrometric analysis of affinity-purified proteasomes.

All patents, published applications and references mentioned throughout this specification are hereby incorporated herein by reference.

EXAMPLES

Example 1

The methods and systems provided are particularly useful for the early detection of mastitis and monitoring or treatment for various milk producing animals such as the dairy cow. However, the methods are broadly applicable to other organisms, including human, and to other conditions such as malignant growth and pathology. The method involves detecting the abundance and activity of the ubiquitin/proteasome pathway in a sample of unprocessed (raw) milk, wherein an increase in proteasome activity in the sample, as compared to a control, is indicative of mastitis. The invention also includes detecting the level of ancillary proteins of the ubiquitin/proteasome pathway and of the immunoproteasome. In a different embodiment of this Invention the mRNA expression of components of the ubiquitin/proteasome pathway will be measured using variations of polymerase chain reaction-based amplification. Oligonucleotide-based detection of released nuclear DNA from somatic cells is also envisioned. There has been no prior description of a measurement of the activity of the ubiquitin/proteasome pathway in milk or utility of such an approach for detecting mastitis.

A kit that will permit early detection, routine monitoring of milk quality, and surveillance of animals that are recovering following illness has also been proposed as a part of this invention. The ability to monitor milk quality and animal health can have a direct positive effect on animal welfare and husbandry. Furthermore, a diagnostic kit developed from the invention will be applied on-site at milking facilities. While this technology and methodology can monitor milk quality and animal welfare, its applicability is not restricted to the dairy industry. The Invention is highly novel, and broadly applicable to all mammals that are of commercial interest and personal value. For instance, other farm animals (including goat, sheep and horse), and animals of non-commercial value (pets) can also suffer from mastitis. Mastitis is a medical concern in the lactating woman, and the Invention can be readily adapted to the nursing mother. The applicability of this invention was verified for monitoring the quality of dairy milk, and following the drug response of infected dairy cows. The invention provides a mechanism to monitor efficacy of drug regimen, and recovery of the animal.

Mastitis is an inflammatory response, which can cause the release of somatic cells into the milk, possibly through lesions in the lining of the udder. Because systemic inflammation involves activation of white blood cells, we envisioned that a significant fraction of the somatic cells in the milk represent cow white blood cells. In earlier studies proteasome activity had been detected in blood cells. However, detection of white blood cells or proteasome activity in raw whole milk has not been envisaged or demonstrated by direct or indirect experiments to date. We were also unable to determine upfront whether the milk can be used in its native raw state or if it needed to be purified to remove other interfering components so that a reliable and accurate determination of the proteasome and related assays could be carried out. It was recognized that milk contains high levels of lipid micelles, and proteins including casein. We were unaware of any high sensitive enzymatic assays for analyzing raw milk, since the turbidity caused by scattering of light by the colloidal particles in the milk emulsion precludes most biochemical measurements. Therefore, we were set out to experiment whether proteasome activity would be detectable in bulk milk. Our experimental findings demonstrate that proteasome activity can be measured in whole raw milk, without a prior need for purifying somatic cells.

In contrast, performing a somatic cell count (SCC) requires specialized instruments, and cannot be performed by straightforward microscopy, because turbidity and light scattering by the milk suspension interferes with the visual inspection of the somatic cells. Furthermore, large aggregates of casein and lipid vesicles prevent clear visualization of the somatic cells. Consequently, the SCC is determined by external laboratories and the dairy farm is not informed of the results for several weeks or months.

This delay provides no benefit to the dairy farmer for monitoring, identifying, quarantining and restoring an infected animal to the milk line. Moreover, the presence of a single infected animal greatly increases the probability of cross-contamination and infection of other animals. Note that the same vacuum tubes are used for collecting milk from many cows, and inadequate treatment with disinfectant will contaminate the next cow that is tethered to the lines.

We specifically detected high levels of a proteasome variant, called the 'Immunoproteasome' in mastitis affected milk. This form of the proteasome contains distinct subunits, and is specifically required for the immune response, consistent with the inflammation that accompanies mastitis.

We also carried out experiments (affinity purification and immunological methods) to define the abundance and activity of various proteasome isoforms. We determined that the higher proteasome activity in mastitis milk was due to increased expression of proteasomes, and proteasome-isoforms. As noted above, we detected high levels of the 'Immunoproteasome', which is specifically activated in response to infection and injury. This finding provides a powerful way to monitor the onset, progression and remission of inflammation, using a straightforward antibody-based assay, which will complement the activity measurement.

In total, the detection of proteasome level may be achieved by measuring both proteasome activity and abundance. The 26S proteasome and its component 19S and 20S particles may be detected. The 'Immunoproteasome' and the associated PA28/13S complex, and novel 20S catalytic particle may also be the subject of a test assay. Regulatory factors that form transient interactions with the proteasome including, but not restricted to, eEF1A, Hsp70, E2 and E3 enzymes, Sts1, Centrin and the family of UbL/UBA shuttle factors (Rad23, Dsk2, Ddi1, etc), and multi-ubiquitinated proteins that are degraded by the proteasome can also be used in such assays.

These assays provide measurements for mastitis that is both sensitive and quantitative. Moreover, these assays can be performed in the field, as it can be developed into a simple kit. These key advances address the critical deficiencies of the current methods, because the Invention detects inflammation before physical manifestation of mastitis is observed, and the assay can be performed on-site. Therefore, an early detection method is envisioned that will overcome the deficiencies in the current methods. In dairy farms milk from a large number of cows is collected in a common reservoir. It is therefore critical to detect infected animals and to remove them from the milk line, before the quality of the milk in the common reservoir has deteriorated. This is not possible with either SCC or the CMT assay. CMT is non-quantitative, and SCC results are provided weeks after sampling. In contrast, our Invention will detect infected milk originating from fewer that $1/100$ infected animals, and the results can be provided in minutes. Thus, the presence of a single infected animal can be initially detected by testing the bulk reservoir. Based on the outcome of the test, the offending animal can be identified, withdrawn and treated. The outstanding sensitivity of our assay stands in contrast to the high SCC level that is permitted in unprocessed whole milk. (Maximum ~750,000 SCC/ml; typical bulk reservoir averages >200,000 SCC/ml. High quality farms may achieve levels below ~40,000 SCC/ml). Thus, the Invention provides extraordinary sensitivity, wherein, high proteasome activity in milk, caused by a single infected animal, will be readily detected in the bulk reservoir. Once the affected animal is identified, the invention allows quantitatively monitoring treatment and recovery, and assisting the farmer in returning the cow to the milk line.

While some embodiments embrace detecting the level of Ub/proteasome pathway or ancillary protein, other embodiment embrace detecting the activity of such proteins. As exemplified herein, an increase in Ub/proteasome pathway proteins is correlated with an increase in proteasome activity. Accordingly, proteasome activity, e.g., as determined using a fluorogenic substrate such as SUC-LLVY-AMC or detection of multiubiquinated proteins, can also be used for pre-clinical detection of mastitis.

Experimental Design and Results

Proteasome Activity in Raw Milk

Raw milk samples were obtained from a local farm once a week for 16 consecutive weeks. Samples (~30 ml) were collected from the daily first milking (~5:00 am) and then stored on ice. All samples were collected by 8:30 am, and processed for proteasome activity by 10:30 am. Proteasome activity was determined at 37° C. with the fluorogenic substrate Suc-LLVY-AMC (SEQ ID NO:2), and quantified using a Turner 7000 fluorometer. Overall protein concentration is highly uniform, and reflects the very high levels of casein and other abundant milk proteins. Therefore, a volume-based assay is most reliable.

In the first set of seven columns, the level of proteasome activity is measured in triplicate from samples taken from the bulk reservoir (maintained at 10° C.). Milk in this reservoir represents the collective output from ~50 cows. Typically, the reservoir contained the output of several days of milking. Note the very low levels of proteasome activity in the bulk reservoir (BULK), and relatively consistent values in seven independent samplings. A specific young healthy female (named Sunshine) was sampled twice, on independent occasions, and low proteasome activity was detected. Another individual cow (Dale) was examined one day after calving and it showed high activity that was restored to lower levels over the next two weeks. It is well known that calving results in high SCC levels in the milk. However, this is a transient phenomenon that we can recapitulate. Two independent cows, suffering from mastitis, were examined.

COW1 had very high levels that required antibiotic treatment. Following a single treatment regimen, we examined proteasome activity and detected a precipitous drop to near normal levels. However, treatment was insufficient and proteasome activity increased dramatically over the course of the next week. Treatment was restored, and lower proteasome activity was observed. Note that baseline levels remained elevated. It is significant that failure to monitor treatment response in a quantitative manner results in inadequate treatment, premature return to the milk line, degradation of bulk tank quality, and recurrence of the infection. Neither the SCC nor the CMT assays currently in use can provide these key measurements. In contrast, our Invention will permit rapid, real-time quantitative analysis of milk quality and animal health.

In COW2, rapid onset of mastitis, following injury of one teat, required antibiotic treatment. We followed proteasome activity in this animal over the next two weeks and observed a dramatic decline as the injury/infection receded and the animal was returned to the milk line. Note that baseline levels were elevated compared to Sunshine, and unaffected bulk reservoir levels.

COW3 was termed a 'chronic offender' by the farmer. We examined this animal over the course of several weeks, and as noted by the dairy farmer, this individual had chronic elevated proteasome activity that fluctuated quite widely. This would represent a highly troublesome animal that would need constant monitoring.

COW4 was under watch by the farmer, as an animal with potential pre-clinical mastitis. As suspected, we detected elevated levels, which were restored to the normal range without treatment. These two samples (COW3 and COW4) illustrate the significant difficult of relying on subjective criterion for identifying troublesome animals. Our Invention will provide rapid and quantitative assessment of milk quality and animal health, and remove intuition and guess-work from the decision. The results are set forth in FIG. 1.

Figure 2:
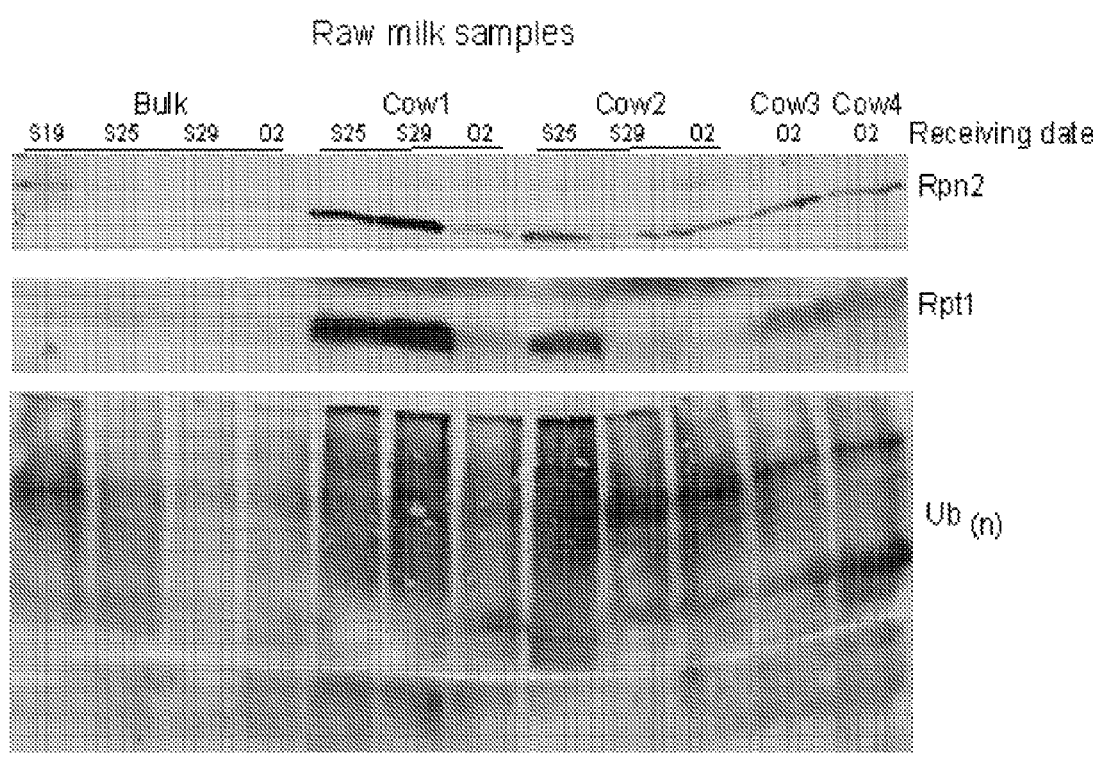
FIG. 2 shows the altered abundance of proteasome subunits.
Figure 2:
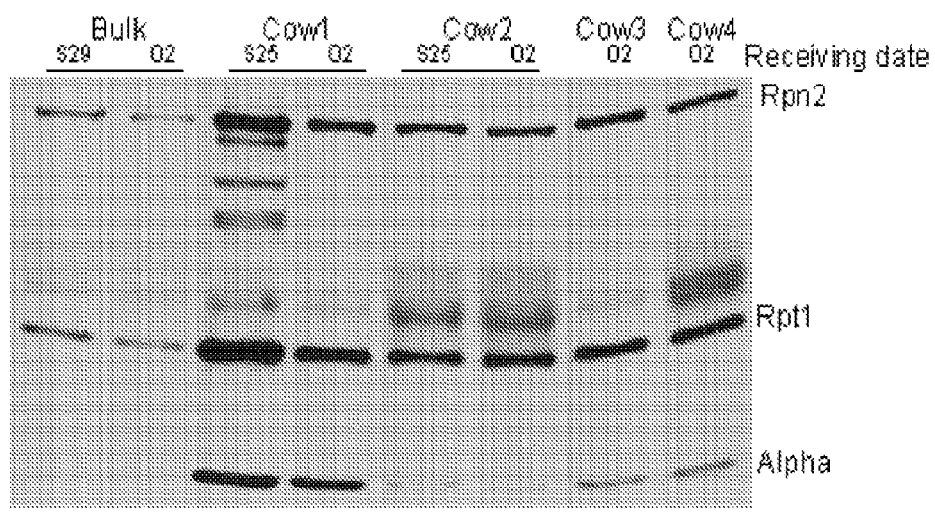

Raw milk samples were separated in SDS-polyacrylamide gels, and the separated proteins were transferred to nitrocellulose. We treated the filters with antibodies against the proteasome subunits Rpn2 and Rpt1, as well as Ub (ubiquitin). We examined milk samples from the Bulk Reservoir, and Cow1, Cow2, Cow3 and Cow4. The samples were acquired on the dates indicated (for example; S19=Sep. 16, 2006). Note that low levels of proteasome subunits and ubiquitin were detected in the Bulk Reservoir, consistent with low proteasome activity (see FIG. 2A). In contrast, Cow1 and Cow2 had significantly elevated amounts of both proteasome subunits and high molecular weight multi-Ubiquitinated proteins, consistent with dramatic increase in proteasome activity (FIG. 2A). The levels of proteasome subunits and ubiquitin cross-reacting material were elevated in Cow3 and Cow4, but not to the same degree as Cow1 and Cow2, again in agreement with the activity measurements (FIG. 2A).

To further verify these results, we purified proteasomes from raw milk, using the UbL (ubiquitin-like) affinity matrix (which we developed and described previously in Lambertson et al. 2003, Current Genetics, Vol. 42, No. 4, 199-208). Highly purified proteasomes were separated in SDS-polyacrylamide gels and examined by immunoblotting. Consistent with the previous panel, we detected higher proteasome levels in Cow1 and Cow2, and more moderate increase in Cow3 and Cow4, entirely consistent with the activity measurements (FIG. 2B).

Figure 3:
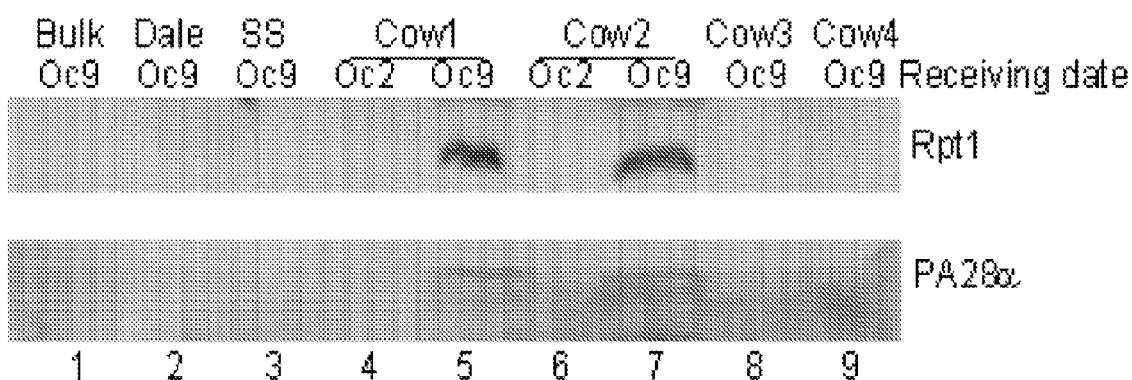
FIG. 3 shows the altered abundance of immunoproteasome subunits.
Figure 3:
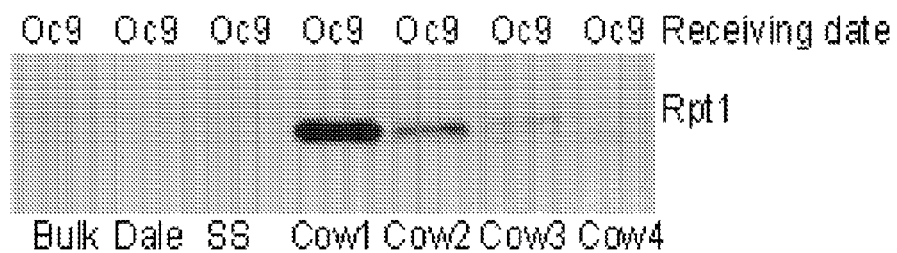

In an independent measurement of proteasome abundance, we retested the levels of the Rpt1 proteasome subunit in raw milk on specific dates for a number of candidate animals. As shown below, a sampling from Oct. 9, 2006, when Cow1 and Cow2 showed dramatically elevated proteasome activity, we also detected a corresponding elevation in the levels of the Rpt1 proteasome subunit. In contrast, Rpt1 was not detected in Bulk tank, Dale, SunShine, or Cow3 and Cow4. Note that on October 9 (see FIG. 3A) both Cow3 and Cow4 had low proteasome activity.

The same immunofilters were reacted with antibodies against the Immunoproteasome subunit PA28α. High levels were observed in Cow1 and Cow2 (lanes 5 and 7), consistent with an immune response that occurs during the inflammatory response following infection and injury.

To confirm that intact proteasomes were present in mastitis milk, we applied 10-fold higher amount of raw milk to UbL matrix to purify proteasomes Immunoblots were examined and Rpt1 was detected in Cow1 and Cow2. Lower amounts were observed in Cow3, and very low levels were detected in Cow4. In contrast, Rpt1 was not detected in Bulk tank, Dale or SunShine. See FIG. 3B.

Figure 4:
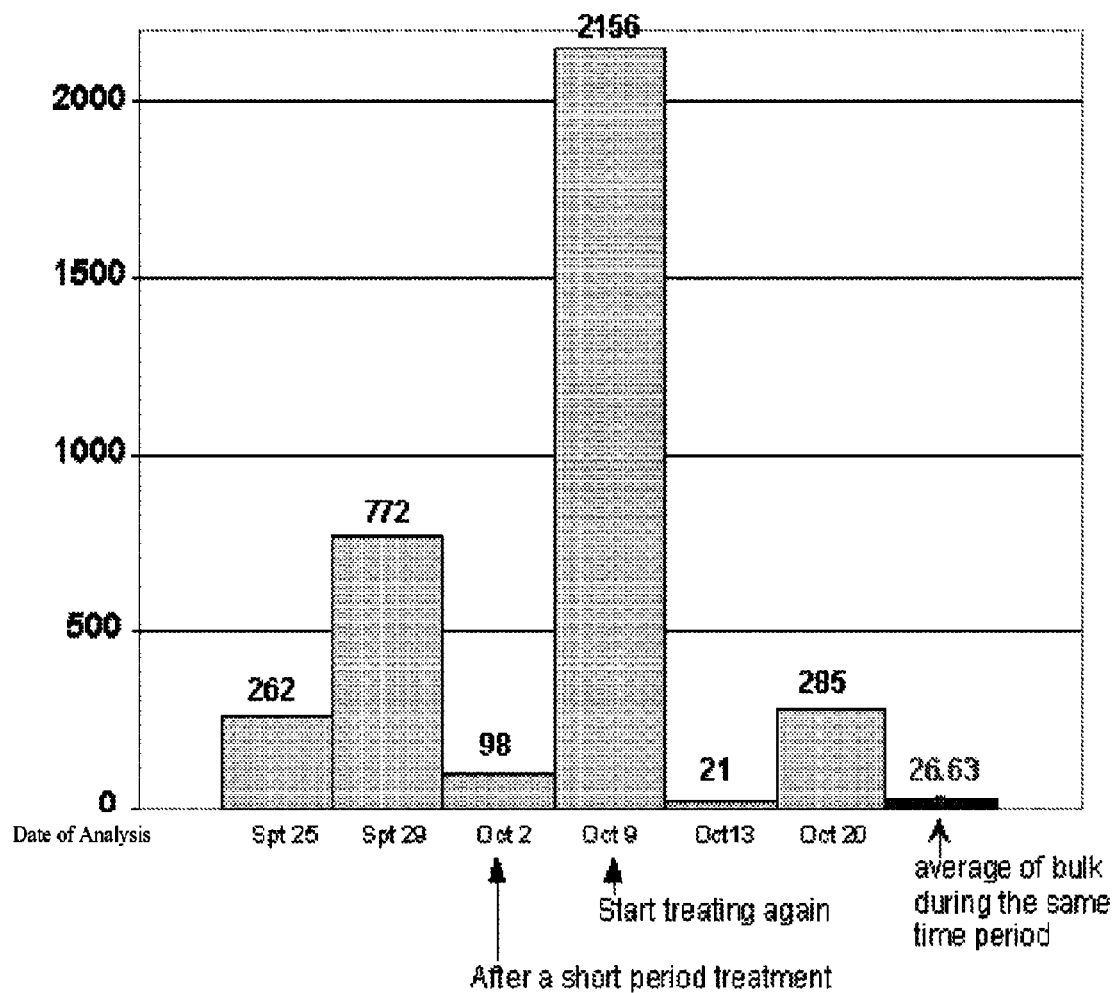
FIG. 4 shows monitoring of proteasome activity.

A careful assessment of an individual cow, chronically infected with mastitis was followed over the course of ~4 weeks. Proteasome activity was compared to the averaged value from the bulk tank, taken at each time point. Note that the average value was 27 units of proteasome activity. The activity in the infected animal ranged 100-fold, from 21 to 2156. Significantly, the animal responded efficiently to treatment with antibiotic (reduced from 2156 to 21), but significantly higher levels were detected within one week following termination of treatment. See FIG. 4.

Example 2

Proteasome activity using fluorogenic peptide substrates to monitor chymotryptic, tryptic and caspase-like activities, proteasome activity using fluorogenic substrates to detect de-ubiquitylation activity, proteasome subunit abundance is determined using high-affinity immunologic methods, the levels of ubiquitin, multi-ubiquitin, and ubiquitinated substrates can be determined using immunologic methods, the assembly of catalytically active 26S proteasomes, from its component 19S and 20S particles, is measured the level of the 'Immunoproteasome' and the associated PA28/13S complex, and novel 20S catalytic particle, is determined using immunologic methods.

Example 3

Measure Proteasome (Chymotryptic) Activity Using Fluorogenic Substrate

Raw milk (50 μl) is suspended in 500 μl lysis buffer (50 mM HEPES, pH 7.5, 150 mM NaCl, 5 mM EDTA and 1% TRITON X-100), lysed by sonication, and total protein quantified using the Bradford assay (BioRad). Protein extracts contain a protease inhibitor cocktail (Roche), to prevent non-proteasomal proteolysis. Protein extracts (20 μg) are characterized in triplicate in a 96-well microtiter plate. Reactions are incubated for 5 min at room temperature, in the presence or absence of the proteasome inhibitors epoxomicin and lactacystin. Proteasome activity is determined by examining the hydrolysis of SUC-LLVY-AMC (SEQ ID NO:2) (Boston Biochem), in 25 mM HEPES pH 7.5, 0.5 mM EDTA. Each reaction, containing 40 μM of SUC-LLVY-AMC (SEQ ID NO:2), is incubated for 1 h at 30° C., and the fluorescence signal quantified over time using a TECAN Infinite F200 plate reader. Proteasome activity is calculated after subtracting non-specific activity that is insensitive epoxomicin-sensitive hydrolysis. Steady-state and kinetic measurements are obtained.

Example 4

Measure Proteasome Abundance Using Antibodies

Protein extract prepared from whole milk is incubated with GST-UbL SEPHAROSE to isolate catalytically active proteasomes. This proprietary reagent was developed by CellXplore. The UbL protein domain (isolated from human Rad23 proteins), forms a high-affinity interaction with catalytically active proteasomes. This efficient affinity matrix provides the only known way to isolate functional proteasomes within ~15 minutes. The activities of the proteasome can be determined while bound to the UbL matrix. The activity of the purified proteasomes is tested as described above. The beads are washed 3 times with 1 ml lysis buffer containing 1% TRITON X-100. Proteasome hydrolytic activity is measured on the immobilized proteaseome. The immobilized proteins are separated in 10% SDS-tricine polyacrylamide gels, transferred to nitrocellulose, and antibodies used to detect the levels of Rptl and Rpnl in the 19S regulatory particle, and the alpha-7 subunit in the 20S catalytic particle.

Example 5

Peptide Substrates

The P4 position from the cleavage site is important for the ability of the proteasome hydrolytic activity to recognize a substrate. This implied that there is a length constraint that must be met to generate an ideal proteasome substrate. Many different residues can be tolerated at the P4 position, although differences in cleavage efficiency can be detected. Proteasome substrates include the tripeptide based Suc-LLVY-AMC (SEQ ID NO:2), and the eight-residue long Suc-RPF-HLLVY-AMC (SEQ ID NO:1). The amino-terminus is generally blocked using succinimide, acetate, vinyl and phenyl groups. For other peptide substrates, see list below.

Ac-nLPnLD-AMC (SEQ ID NO:6)—Fluorogenic Substrate for Caspase-like Activity

Ac-Arg-Leu-Arg-AMC—Proteasome Substrates for Trypsin-like Activity

Ac-GPLD-AMC (SEQ ID NO:7)—Fluorogenic Substrate Proteasome Substrates for Caspase-like Activity Boc-LRR-AMC—Fluorogenic Substrate for Trypsin-like Activity Bz-VGR-AMC—Fluorogenic Substrate for Trypsin-like Activity MCMV pp 89 20S Proteasome Substrate Peptide Proteasome Substrates for All Activities;

Suc-LLVY-AMC (SEQ ID NO:2) Fluorogenic Substrate

Suc-RPFHLLVY-AMC (SEQ ID NO:1), Fluorogenic Substrate for Chymotrypsin-like Activity Z-GGL-βNA, Fluorogenic Substrate for Chymotrypsin-like Activity Z-GGL-AMC, Fluorogenic Substrate for Chymotrypsin-like Activity Z-LLE-βNA, Fluorogenic Substrate for Caspase-like Activity Z-LLE-AMC, Fluorogenic Substrate for Caspase-like Activity Example 6

Figure 5:
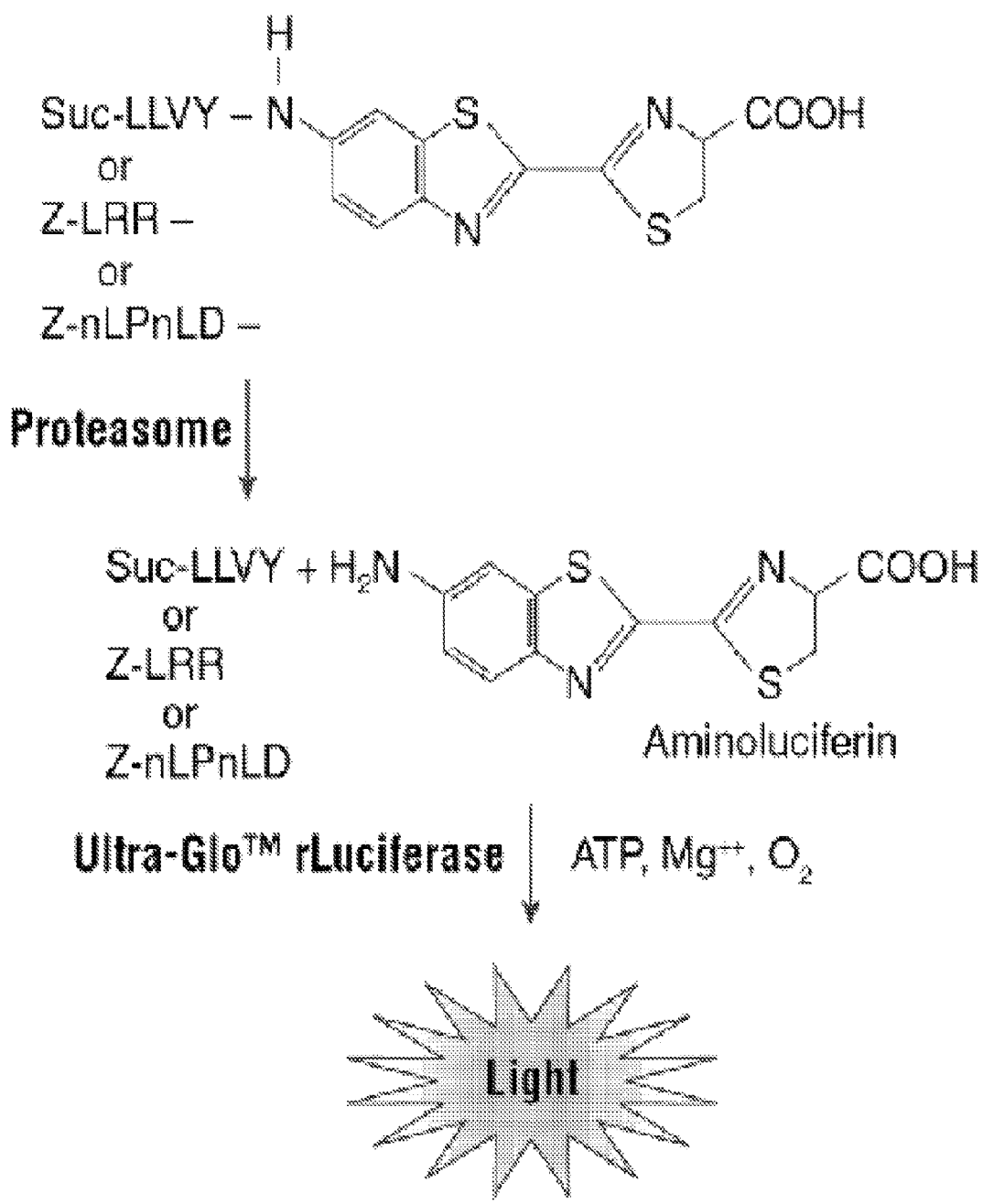
FIG. 5 shows a depiction of examples of luminescent assays.

In addition to the commonly used fluorogenic assay using for example AMC, a luminescent assay using the firefly luciferase enzyme is also available using commercially available materials and well-known techniques. Examples of luminescent assays (Promega Inc) include the reaction set forth in FIG. 5.

Example 7

Antibodies against specific subunits are available commercially. Antibodies listed in the table in FIG. 6 are available from BioMol. Antibodies that may be used in an immunoprecipitation (IP) reaction are expected to recognize the intact, functionally active proteasome. Note that Rpn10 and Rpn12 could both be used. Similarly, numerous alpha- and beta-subunits in the 20S catalytic particle may be targeted with antibodies for immunoprecipitation reactions. These antibodies may also be used in ELISA-based assays.

Example 8

A set of ~12 non-fluorogenic substrates that required at least two different targeting pathways were described by Bachmair and Varshaysky Cell, Vol 56, 1019-1032, 24 Mar. 1989. These reporter substrates contained the E. coli beta-galactosidase enzyme, and their degradation could be demonstrated in bacteria, human and metazoans (including human cultured cells). More recent derivatives include degradation substrates based on glutathione-S-transferease, and green fluorescence protein. Additionally, there are by now dozens, if not hundreds, of physiological substrates of the Ub/proteasome pathway. Access to the interior of the proteasome (which contains the three catalytic activities) is restricted by a narrow (13 angstrom) translocation channel.

Example 9

A test-strip may contain different amounts of an antibody that recognizes a specific proteasome subunit. Exposure of the strip to milk containing proteasomes (as in mastitis) would result in binding to the immobilized antibody. The proteasome subunit would then be detected using a second antibody that recognizes the same protein. However, the second antibody would be coupled to a marker that permits detection. Microfluidics, lateral flow devices and in-line (real-time) sensors, are all amenable to this approach.

1. Conjugation of the second antibody to horse radish peroxidase (HRP) could be used to generate a colorimetric or chromogenic signal. However, the antibody could be conjugated to any enzyme whose activity can be measured.

2. The second antibody could be coupled to a magnetic bead that could be detected by incubation with metal particles coated with FITC (for a fluorescence readout).

The second antibody could be coupled to biotin, and the reaction developed using strepavidin conjugated to FITC or other easily detected fluorescence markers.

In another embodiment of this approach, whole (raw) milk could be directly incubated with a test-strip containing a small patch (or patches) of nitrocellulose, or other high-affinity protein binding surfaces. The strip would then be incubated with an antibody against a specific proteasome subunit, and detected as described above.

Example 10

In some embodiments, the proteasome level is tested from samples obtained from a bulk storage tank containing milk from a plurality of animals.

In some embodiments, the proteasome level is tested from samples obtained from a sample of milk from a single animal. Such samples may be tested as part of a routine testing program, or when the dairyman suspects that the animal may have an infection. In such cases, pre-clinical mastitis may be diagnosed prior to the appearance of any symptoms of inflammation and monitoring may be increased or the treatment of such animals may begin. Samples of milk from a single anima may be tested in cases where a diagnosis of mastitis has been previously made and treatment undertaken. Testing informs the dairyman if the animals condition has been resolved or if an low level infection persists. This ensures that treatment can be discontinued and animals may be prepared for return to the line as soon as they are ready but not prematurely when the risk of relapse is great.

The invention claimed is:

1. A method for determining if one or more animals has mastitis, the method comprising
   (a) performing a test assay and thereby determining a level of proteasomes present in a test sample of milk collected from the one or more animals;
   (b) comparing the level of proteasomes present in the test sample with a standard level of proteasomes in a control sample of milk from an uninfected animal; and
   (c) correlating an increased level of proteasomes present in the test sample relative to the standard level of proteasomes present in the control sample as being indicative of the one or more animals having mastitis.

2. The method of claim 1, wherein the test assay detects proteasome activity in the test sample.

3. The method of claim 2, wherein the proteasome activity is measured by measuring a level of conversion of a proteasome enzyme substrate to a product.

4. The method of claim 3, wherein the proteasome enzyme substrate is selected from the group consisting of Suc-Arg-Pro-Phe-His-Leu-Leu-Val-Tyr-AMC (SEQ ID NO:1); Z-Gly-Gly-Leu-betaNA; Z-Gly-Gly-Leu-AMC; Suc-Leu-Leu-Val-Tyr-AMC (SEQ ID NO:2); Suc-Leu-Tyr-AMC; Ac-Arg-Leu-Arg-AMC; Boc-Leu-Arg-Arg-AMC; Bz-Val-Gly-Arg-AMC; Ac-Gly-Pro-Leu-Glu-AMC (SEQ ID NO:3); Z-Leu-Leu-Asp-AMC; Z-Leu-Leu-Asp-betaNA; and Ac-nLeu-Pro-nLeu-Glu-AMC (SEQ ID NO:4); wherein Suc refers to succinimide; AMC refers to 7-amino-4-methylcoumarylamide; Z refers to benzyloxycarbonyl; betaNA refers to beta-naphthylamide; Boc refers to tert-butyloxycarbonyl; Bz refers to benzoyl; Ac refers to acetyl; and nLeu refers to norleucinal.

5. The method of claim 3, which can distinguish eukaryotic proteasomes from prokaryotic proteasomes.

6. The method of claim 3, wherein the proteasome enzyme substrate is an ATPase substrate.

7. The method of claim 3, wherein the proteasome enzyme substrate is a de-ubiquitinase substrate.

8. The method of claim 1, wherein the test assay comprises an assay selected from the group consisting of protein detection and detection of nucleic acid molecules that encode proteins.

9. The method of claim 8, wherein the test assay detects one or more molecules selected from the group consisting of one or more proteasome proteins; one or more proteasome-binding proteins; one or more proteasome-regulating proteins; and a nucleic acid molecule that encodes a proteasome protein, a proteasome-regulating protein or a proteasome-binding protein.

10. The method of claim 8, wherein the test assay comprises an assay to determine a level of immunoproteasomes present in the test sample.

11. The method of claim 8, wherein the test assay comprises an assay to detect a level of ubiquinated proteins in a sample or an assay to detect copper-complex binding to proteasomes.

12. A method for determining milk quality, the method comprising
   (a) collecting a test sample of milk;
   (b) performing a test assay and thereby determining a level of proteasomes present in the test sample;
   (c) comparing the level of proteasomes present in the test sample with a first standard level of proteasomes in a first control sample of high quality milk, or comparing the level of proteasomes present in the test sample with a second standard level of proteasomes in a second control sample of low quality milk; and
   (d) making at least one of the following correlation steps:

(i) correlating an increased level of proteasomes present in the test sample relative to the first standard level of proteasomes as being indicative of the test sample being milk of lower quality than the first control sample of high quality milk;
(ii) correlating an increased level of proteasomes present in the test sample relative to the second standard level of proteasomes as being indicative of the test sample being milk of higher quality than the second control sample of low quality milk;
(iii) correlating a substantially similar level of proteasomes present in the test sample relative to the first standard level of proteasomes as being indicative of the test sample being milk of high quality; and
(iv) correlating a substantially similar level of proteasomes present in the test sample relative to the second standard level of proteasomes as being indicative of the test sample being milk of low quality.

\* \* \* \* \*